US006222027B1

(12) United States Patent
Kaser et al.

(10) Patent No.: US 6,222,027 B1
(45) Date of Patent: Apr. 24, 2001

(54) MOLECULES EXPRESSED IN HIPPOCAMPUS

(75) Inventors: Matthew R. Kaser, Castro Valley; Preeti Lal, Santa Clara; Henry Yue, Sunnyvale; Y. Tom Tang, San Jose; Mariah R. Baughn, San Leandro; Yalda Azimzai, Hayward, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/313,300

(22) Filed: May 17, 1999

(51) Int. Cl.[7] .................................................... C07H 21/02
(52) U.S. Cl. ...................... 536/23.1; 536/23.1; 536/23.5; 536/25.1; 536/24.31; 514/2; 514/12; 435/69.52; 435/252.3; 435/7.1; 435/6; 435/320.1; 435/7.2; 435/91.3; 435/803; 530/350; 530/300; 530/387.1; 436/94; 436/808; 436/811; 436/501
(58) Field of Search ................................ 435/69.52, 252.3, 435/7.1, 320.1, 7.2, 6, 91.3, 803; 530/387.1, 350, 300; 536/23.5, 23.1, 25.1, 24.31; 436/501, 548, 94, 808, 811; 514/2, 12

(56) References Cited

U.S. PATENT DOCUMENTS 5,962,261 * 10/1999 Hillman et al. ..................... 435/69.1

FOREIGN PATENT DOCUMENTS

WO99/06548 * 8/1997 (WO).

OTHER PUBLICATIONS

Doerks et al., TIG, vol. 14, No. 6, pp. 248–249, Jun. 1998.*

Jack, C.R., Jr., "MRI–Based Hippocampal Volume Measurements in Epilepsy," *Epilepsia*, 35:S21–S29 (1994).

Sapolsky, R.M., "Potential behavioral modification of glucocorticoid damage to the hippocampus," *Behavioural Brain Res.*, 57:175–182 (1993).

Hillier et al. (Direct Submission), Accession No. AA434549 (see alignment), 1997.*

NCI/NINDS–CGAP (Direct Submission), Accession No. AI088762 (see alignment), 1995.*

* cited by examiner

*Primary Examiner*—Christopher S. F. Low
*Assistant Examiner*—Hope A. Robinson
(74) *Attorney, Agent, or Firm*—Incyte Genomics, Inc.

(57) ABSTRACT

The invention provides novel developmentally-regulated hippocampal genes and polypeptides encoded by those genes. The invention also provides expression vectors, host cells, and antibodies. The invention also provides methods for diagnosing, treating or preventing diseases associated with hippocampus.

6 Claims, 3 Drawing Sheets

```
                10          19          28       37          46      55
5' CCAG GCA CCT GAC GCC TCT TTC CCC TCA CGG TGC CAG GGC CGG GCC GAA CTA CAT 64          73          82       91          100     109
TTC CCA GGA GGC TCC GCG GCC AGG TGC AAA CAG CGC CGT GCT GAC TAC ATT TCC 118         127         136      145         154     163
CAG ACA GCC TTG CGG CCC GGG CCT TAA AGC GTC CAT TTC CCA GCG GCC CTC 172         181         190      199         208     217
CGC TGC GAG ACC GCA GCC CTT CTC TGG AGT CTC AGA GCC GCA AGA CAC GAC 226         235         244      253         262     271
TCC CAG AGG ACC TTG CGT CGG GCA AGA AAG ACT ACA CCT TCC AGG CTC TGC 280         289         298      307         316     325
GGC GCC GCG ACA GGA AGC GGG GGG CGA GCC GAG TGT CCT TGC GCG TGG ATC CGA
```

FIGURE 1A

```
     334              343              352              361              370              379
GCG ACC ATG GTG GCC CGG GTG TGG TCG CTG ATG AGG TTC CTC ATC AAG GGA AGT
 A   T   M   V   A   R   V   W   S   L   M   R   F   L   I   K   G   S 388              397              406              415              424              433
GTG GCT GGG GGC GCC GTC TAC CTG GTG TAC GAC CAG GAG CTG GGG CCC AGC
 V   A   G   G   A   V   Y   L   V   Y   D   Q   E   L   G   P   S 442              451              460              469              478              487
GAC AAG AGC CAG GCA CTA CAG AAG GCT GGG GAG GTG GTC CCC CCC GCC ATG
 D   K   S   Q   A   L   Q   K   A   G   E   V   V   P   P   A   M 496              505              514              523              532              541
TAC CAG TTC AGC CAG TAC GTG TGT CAG CAG ACA GGC CTG CAG ATA CCC CAG CTC
 Y   Q   F   S   Q   Y   V   C   Q   Q   T   G   L   Q   I   P   Q   L 550              559              568              577              586              595
CCA GCC CCT CCA AAG ATT TAC TTT CCC ATC CGT GAC TCC TGG AAT GCA GGC ATC
 P   A   P   P   K   I   Y   F   P   I   R   D   S   W   N   A   G   I
```

FIGURE 1B

```
      604             613         622         631         640         649
ATG ACG GTG ATG TCA GCT CTG TCG GTG GCC CCC TCC AAG GCC CGC GAG TAC TCC
 M   T   V   M   S   A   L   S   V   A   P   S   K   A   R   E   Y   S 658             667         676         685         694         703
AAG GAG GGC TGG GAG TAT GTG AAG GCG CGC ACC AAG TAG CGA GTC AGC AGG GGC
 K   E   G   W   E   Y   V   K   A   R   T   K 712             721         730         739         748         757
CGC CTG CCC CGG CCA GAA CGG GCA GGG CTG CCA CTG ACC TGA AGA CTC CGG ACT 766             775         784         793         802         811
CGG ACC CCA CTC CGA GGG CAG CTC CCG GCC TTG CCG GCC CAA TAA AGG ACT TCA 820             829
GAA GTG TAA AAA AAA AAA  3'
```

FIGURE 1C

MOLECULES EXPRESSED IN HIPPOCAMPUS

FIELD OF THE INVENTION

The present invention relates to polynucleotides comprising at least a fragment of genes expressed in hippocampus. The invention also relates to the use of these molecules in diagnosis, prognosis, prevention, treatment, and evaluation of therapies for diseases associated with the hippocampus such as Alzheimer's disease, Huntington's disease, schizophrenia, epilepsy, and their complications.

BACKGROUND OF THE INVENTION

The hippocampus is part of the brain's limbic system which controls emotional behavior, motivational drive, and other physiological functions. The limbic system includes the limbic cortex, hippocampus, amygdala, hypothalamus, and anterior thalamus. The hippocampus plays an important role in learning processes and certain types of memory. Stimulation of the hippocampus can cause behavioral responses including rage, passivity, and excess sex drive. Weak electrical stimulation can cause hippocampal seizures. Individuals who lose hippocampal function retain memory for events that occurred prior to the loss and only have immediate memory, lasting less than a few minutes, for all events after the loss (anterograde amnesia). Thus, the hippocampus is thought to interpret the importance of incoming sensory information and to determine what input is worth remembering. The hippocampus then transmits signals that make the mind rehearse the information over and over again until permanent storage takes place.

Numerous studies of the effects of ablation of the hippocampus of rodent, primate, and other non-human species have been conducted. Memory disorders and spatial performance are associated with hippocampal function. Morphological changes in the hippocampus, including cell loss, is associated with epilepsy, schizophrenia, Alzheimer's disease, and certain amnesiac syndromes. (Jack (1994) *Epilepsia* 35:S21–S29). Research data from animals show glucocorticoids secreted during stress can damage the hippocampus and impair the ability of hippocampal neurons to survive neurological insults. (Sapolsky (1993) *Behav. Brain Res.* 57:175–82). Sustained glucocorticoid exposure might damage the hippocampus in humans as well; hippocampal atrophy has been reported in patients with Cushing's syndrome as a result of the hypersecretion of glucocorticoids.

Phylogenetic relationships among organisms have been demonstrated many times, and studies from a diversity of prokaryotic and eukaryotic organisms suggest a more or less gradual evolution of biochemical and physiological mechanisms and metabolic pathways. Despite different evolutionary pressures, proteins that regulate the cell cycle in yeast, nematode, fly, rat, and man have common chemical or structural features and modulate the same general cellular activity. Comparisons of human gene sequences with those from other organisms where the structure and/or function may be known allow researchers to draw analogies and to develop model systems for testing hypotheses. These model systems are of great importance in developing and testing diagnostic and therapeutic agents for human conditions, diseases and disorders.

Identification of genes that participate in hippocampal development provide new potential diagnostic and therapeutic targets. The present invention satisfies a need in the art by providing new compositions that are useful for diagnosis, prognosis, treatment, prevention, and evaluation of therapies for diseases associated with hippocampus such as Alzheimer's disease, Huntington's disease, schizophrenia, epilepsy, and their complications.

SUMMARY OF THE INVENTION

In one aspect, the invention provides for substantially purified polynucleotides expressed in hippocampus. Preferred embodiments include (a) a polynucleotide sequence of SEQ ID NOs:1–7; (b) a polynucleotide sequence which encodes the polypeptide sequence of SEQ ID NO:8; (c) a polynucleotide sequence having at least 70% identity to the polynucleotide sequence of (a) or (b); (d) a polynucleotide sequence which is complementary to the polynucleotide sequence of (a), (b), or (c); (e) a polynucleotide sequence comprising at least 10, preferably at least 18, sequential nucleotides of the polynucleotide sequence of (a), (b), (c), or (d); and (f) a polynucleotide which hybridizes under stringent conditions to the polynucleotide of (a), (b), (c), (d) or (e). Furthermore, the invention provides an expression vector comprising any of the above described polynucleotides and host cells comprising the expression vector. Still further, the invention provides a method for treating or preventing a disease or condition associated with the altered expression of a gene that is expressed in hippocampus comprising administering to a subject in need a polynucleotide described above in an amount effective for treating or preventing the disease.

In a second aspect, the invention provides a substantially purified polypeptide comprising the gene product of a gene that is expressed in hippocampus. Preferred embodiments are (a) the polypeptide sequence of SEQ ID NO:8; (b) a polypeptide sequence having at least 85% identity to the polypeptide sequence of (a); and (c) a polypeptide sequence comprising at least 6 sequential amino acids of the polypeptide sequence of (a) or (b). Additionally, the invention provides antibodies that bind specifically to the above described polypeptide and a method for treating or preventing a disease or condition associated with the altered expression of a gene that is expressed in hippocampus comprising administering to a subject in need such an antibody in an amount effective for treating or preventing the disease.

In another aspect, the invention provides a pharmaceutical composition comprising any one of the polynucleotides or polypeptide described above in conjunction with a suitable pharmaceutical carrier and a method for treating or preventing a disease or condition associated with the altered expression of a gene that is expressed in hippocampus comprising administering to a subject in need such a composition in an amount effective for treating or preventing the disease.

In a further aspect, the invention provides a method for diagnosing a disease or condition associated with the altered expression of a gene that is expressed in hippocampus. The method comprises the steps of (a) providing a sample comprising one or more of the expressed genes; (b) hybridizing one or more of the polynucleotides described above to the expressed genes under conditions effective to form one or more hybridization complexes; (c) detecting the hybridization complexes; and (d) comparing the levels of the hybridization complexes with the level of hybridization complexes in a nondiseased sample, wherein altered levels of one or more of the hybridization complexes in a diseased sample compared with the level of hybridization complexes in a non-diseased sample correlates with the presence of the disease or condition.

The invention also provides a method for using a nucleic acid sequence or a fragment thereof to screen a library of molecules to identify at least one molecule which specifically binds the nucleic acid sequence, the method comprising providing a library of molecules, combining the nucleic acid sequence with the library of molecules under conditions suitable to allow specific binding, and detecting specific binding, thereby identyfying a molecule which specifically binds the nucleic acid sequence. Such libraries include DNA and RNA molecules, peptides, PNAs, proteins, and the like which are potential regulators of replication, transcription, and translation. The invention also provides a method for using a protein or a portion thereof to screen a library of molecules to identify at least one molecule which specifically binds the protein, the method comprising providing a library of molecules, combining the protein with the library of molecules under conditions suitable to allow specific binding, and detecting specific binding, thereby identifying a molecule which specifically binds the protein. In one aspect, a molecule identified using the method modulates the activity of the protein.

Additionally, the invention provides antibodies, antibody fragments, and immunoconjugates that exhibit specificity to the above described polypeptide and methods for treating or preventing a disease or condition associated with hippocampus.

BRIEF DESCRIPTION OF THE SEQUENCE LISTING

The Sequence Listing provides exemplary sequences of genes expressed in adult rat hippocampus, SEQ ID NOs:9–15, and homologous human sequences including polynucleotide sequences, SEQ ID NOs:1–7, and polypeptide sequence, SEQ ID NO:8. Each sequence is identified by a sequence identification number (SEQ ID NO) and by the Incyte Clone number with which the sequence was first identified.

Table 1 shows the Incyte clone number for nucleic acid sequences expressed in adult rat hippocampus but absent from fetal rat hippocampus; the Incyte clone number and SEQ ID NO: for the human nucleic acid homolog; the location of a unique region of the human nucleic acid sequence; the sequence identity between the rat sequence and corresponding human sequence; and the tissues where the human sequence is predominantly expressed.

FIGS. 1A, 1B, and 1C show the nucleic acid sequence of SEQ ID NO:7 and encoded amino acid sequence, SEQ ID NO:8. The alignment was produced using MACDNASIS PRO software (Hitachi Software Engineering, South San Francisco Calif.).

DESCRIPTION OF THE INVENTION

It must be noted that as used herein and in the appended claims, the singular forms "a", "an" and "the" include the plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Definitions

"NSEQ" refers generally to a polynucleotide sequence of the present invention, including SEQ ID NOs:1–7. "PSEQ" refers generally to a polypeptide sequence of the present invention, including SEQ ID NO:8.

A "fragment" can refer to a nucleic acid sequence that is preferably at least 20 nucleic acids in length, more preferably 40 nucleic acids, and most preferably 60 nucleic acids in length, and encompasses, for example, fragments consisting of nucleic acids 1–50, 51–400, 401–4000, 4001–12,000, and the like, of SEQ ID NOs:1–7.

"Gene" or "gene sequence" refers to the partial or complete coding sequence of a gene, its complement, and its 5' or 3' untranslated regions.

"Homology" refers to sequence similarity between a reference sequence and at least a fragment of a newly sequenced clone insert or its encoded amino acid sequence.

"Polynucleotide" refers to a nucleic acid, nucleic acid sequence, oligonucleotide, nucleotide, or any fragment thereof. It may be DNA or RNA of genomic or synthetic origin, double-stranded or single-stranded, and combined with carbohydrate, lipids, protein or other materials to perform a particular activity or form a useful composition. "Oligonucleotide" is substantially equivalent to the terms amplimer, primer, oligomer, element, and probe.

"Polypeptide" refers to an amino acid, amino acid sequence, oligopeptide, peptide, or protein or portions thereof whether naturally occurring or synthetic.

A "portion" refers to an amino acid sequence which is preferably at least 5 to about 15 amino acids in length, most preferably at least 10 amino acids long, and which retains some biological or immunological activity of, for example, SEQ ID NO:8.

"Sample" is used in its broadest sense. A sample containing nucleic acids may comprise a bodily fluid; an extract from a cell, chromosome, organelle, or membrane isolated from a cell; genomic DNA, RNA, or cDNA in solution or bound to a substrate; a cell; a tissue; a tissue print; and the like.

"Substantially purified" refers to a nucleic acid or an amino acid sequence that is removed from its natural environment and that is isolated or separated, and is at least about 60% free, preferably about 75% free, and most preferably about 90% free, from other components with which it is naturally present.

"Substrate" refers to any suitable rigid or semi-rigid support to which polynucleotides or polypeptides are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

A "variant" refers to a polynucleotide or polypeptide whose sequence diverges from SEQ ID NOs:1–7 or SEQ ID NO:8, respectively. Polynucleotide sequence divergence may result from mutational changes such as deletions, additions, and substitutions of one or more nucleotides; it may also be introduced to accommodate differences in codon usage. Each of these types of changes may occur alone, or in combination, one or more times in a given sequence. Polypeptide variants include sequences that possess at least one structural or functional characteristic of SEQ ID NO:8.

Detailed Description

Sequences in the present invention were first identified by comparing polynucleotides expressed in a fetal rat hippocampus-derived cDNA library to polynucleotides expressed in an adult rat hippocampus-derived cDNA library. Since some of the polynucleotide sequences were identified solely based on expression levels, it is not essential to know a priori the function of a particular gene in hippocampus. The abundance sort program of the invention described in U.S. Pat. No. 5,840,484 entitled "Comparative Gene Transcript Analysis", incorporated herein by reference, was used to tabulate and sort by frequency the mRNA transcripts corresponding to each gene identified in rat fetal and adult hippocampal tissues. Comparative gene transcript analysis was then employed to identify genes differentially expressed in adult rat hippocampus but not in fetal rat hippocampus.

After assembling EST clusters, a transcript image for each cDNA library was generated and the frequency or abundance of a given EST cluster was determined. The frequency of an EST cluster in a clone population correlated to the level of expression of a particular gene. Transcript analysis summarized the presence and abundance of exact, unique, and homologous transcripts which were specific to each tissue sample. Polynucleotides expressed only in adult rat hippocampus were used to identify homologous sequences from human. The human nucleic acid sequences, SEQ ID NOs:1–7, the amino acid sequence corresponding to SEQ ID NO:7, SEQ ID NO:8, and the rat nucleic acid sequences, SEQ ID NOs:9–15, are provided in the Sequence Listing.

Table 1 shows the nucleic acid sequences expressed in adult rat hippocampus but absent from fetal rat hippocampus, SEQ ID NOs:9–15, and their human homologs, SEQ ID NOs:1–7. Column 1 lists the Incyte clone number for each nucleic acid sequence, SEQ ID NOs:9–15, expressed in adult rat hippocampus but absent from fetal rat hippocampus first identified. These rat nucleic acid sequences were used to identify the human nucleic acid sequences shown in column 3. Columns 2 and 3 list the SEQ ID NO: and corresponding Incyte clone number, respectively, for each human nucleic acid sequence. Fragments of SEQ ID NOs:1–7 are useful in hybridization or amplification technologies to identify changes in expression pattern of the same or similar sequences. Column 4 shows exemplary fragments for SEQ ID NOs:1–7. Column 5 shows the sequence identity between the rat nucleic acid sequence in column 4 and the corresponding human nucleic acid sequence in column 2. Column 6 identifies the human tissues where the sequences in column 3 are predominantly expressed. All of the human sequences are expressed in nervous tissue, including hippocampus.

Therefore, in one embodiment, the invention encompasses a polynucleotide sequence (NSEQ) comprising the sequence of SEQ ID NOs:1–7. These 7 polynucleotides are shown by the method of the present invention to have strong differential expression association with adult hippocampus. The invention also encompasses a variant of the polynucleotide sequence, its complement, or 18 consecutive nucleotides of a sequence provided in the above described sequences. Variant polynucleotide sequences typically have at least about 70%, more preferably at least about 85%, and most preferably at least about 95% polynucleotide sequence identity to NSEQ.

The invention provides polynucleotide sequences comprising at least a fragment of one or more genes expressed in hippocampus. The polynucleotide sequences are useful for screening libraries of molecules for specific binding and for diagnosis and prognosis of diseases of the hippocampus, such as Alzheimer's disease, Huntington's disease, schizophrenia, epilepsy, and their complications.

The polynucleotide sequences are particularly useful when they are hybridizable array elements in a microarray. Such a microarray can be employed to monitor the expression of genes which are differentially expressed in fetal, normal, diseased, or treated hippocampus. The microarray can be used in large scale genetic or gene expression analysis of a large number of polynucleotide sequences; in the diagnosis of diseases before phenotypic symptoms are evident; or in the differential diagnosis of diseases with similar symptoms. The microarray can also be used in the monitoring and evaluation of treatments where altered expression of genes coding for polypeptides implicated in hippocampus function cause disease, such as epilepsy. Additionally, the microarray can be used to investigate an individual's predisposition to a disease, such as Alzheimer's disease. Furthermore, the microarray can be employed to investigate cellular responses, such as nerve cell proliferation, regeneration, degeneration, and the like.

When the polynucleotide sequences of the invention are employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease, condition, or treatment.

The invention also entails a pharmaceutical composition comprising a polynucleotide sequence of the invention in conjunction with a suitable pharmaceutical carrier and a method for treating or preventing a disease or condition associated with the altered expression of genes that regulate the hippocampus comprising administering to a subject in need such a composition in an amount effective for treating or preventing a disease or condition associated with hippocampus.

After assembling EST clusters, a transcript image for each cDNA library is generated, and the frequency or abundance of a given EST cluster is determined. The frequency of an EST cluster in a clone population is correlated to the level of expression of a particular gene. Transcript analysis summarizes the presence and abundance of exact, unique, and homologous transcripts which are specific to each tissue sample. Comparison of transcript images derived from different biological samples can demonstrate a statistically significant correlation between cell and tissue source information, such as disease states, treatment outcomes, exposure to various environmental factors, genotypes, and the expression levels of particular genes or groups of genes. Comparisons between transcript images of different cells or tissues or of the same cells or tissues under different conditions can be used to discern differences in transcriptional activities. For example, a transcript image may show the following differences: a) differences between brain tissues hippocampus and frontal cortex; b) differences between normal and diseased brain tissue, or c) differences between untreated and treated brain tissue.

Transcript image comparisions can be obtained by methods well known to those skilled in the art. Transcript levels and images can be obtained and compared, for example, by a differential gene expression assay based on a quantitative hybridization of arrayed DNA clones (Nguyen, et al. (1995) *Genomics* 29:207–216), based on the serial analysis of gene expression (SAGE) technology (Velculescu et al. (1995) *Science* 270:484–487), based on the polymerase chain reaction (Peng et al. (1992) *Science* 257:967–971; Prashar et al. (1996) *Proc. Natl. Acad. Sci. USA* 93:659–663), based on a differential amplification protocol (Van Gelder et al. U.S. Pat. No. 5,545,522), or based on electronic analysis, such as comparative gene transcript analysis (Seilhamer et al. U.S. Pat. No. 5,840,484) or the GEMTOOLS gene expression analysis program (Incyte Pharmaceuticals, Palo Alto Calif.). Preferably, comparisons between two or more transcript profiles are performed electronically.

Specifically, transcript profiles can be compared to identify polynucleotide sequences whose transcripts (1) are present only in fetal hippocampus, (2) are present only in adult hippocampus, (3) are expressed at higher levels in fetal hippocampus than in adult hippocampus, (4) are expressed at higher levels in adult hippocampus than in fetal hippocampus, (5) are present in other rat tissue, such as liver, but not present in fetal hippocampus nor adult hippocampus, and (6) are present in both fetal hippocampus and adult hippocampus and show no statistically significant differences in expression when comparing tissues.

NSEQ or the encoded PSEQ may be used to search against the GenBank primate (pri), rodent (rod), mammalian (mam), vertebrate (vrtp), and eukaryote (eukp) databases, SwissProt, BLOCKS (Bairoch et al. (1997) Nucleic Acids Res. 25:217–221), PFAM, and other databases that contain previously identified and annotated motifs, sequences, and gene functions. Methods that search for primary sequence patterns with secondary structure gap penalties (Smith et al. (1992) Protein Engineering 5:35–51) as well as algorithms such as Basic Local Alignment Search Tool (BLAST; Altschul, S. F. (1993) J. Mol. Evol. 36:290–300; Altschul et al. (1990) J. Mol. Biol. 215:403–410), BLOCKS (Henikoff, S. and Henikoff, G. J. (1991) Nucleic Acids Research 19:6565–6572), Hidden Markov Models (HMM; Eddy, S. R. (1996) Cur. Opin. Str. Biol. 6:361–365; Sonnhammer et al. (1997) Proteins 28:405–420), and the like, can be used to manipulate and analyze nucleotide and amino acid sequences. These databases, algorithms and other methods are well known in the art and are described in Ausubel et al. (1997; *Short Protocols in Molecular Biology*, John Wiley & Sons, New York N.Y., unit 7.7) and in Meyers, R. A. (1995; *Molecular Biology and Biotechnology*, Wiley VCH, New York N.Y., p 856–853).

Also encompassed by the invention are polynucleotide sequences that are capable of hybridizing to SEQ ID NOs:1–7, and fragments thereof under stringent conditions. Stringent conditions can be defined by salt concentration, temperature, and other chemicals and conditions well known in the art. Suitable conditions can be selected, for example, by varying the concentrations of salt in the prehybridization, hybridization, and wash solutions or by varying the hybridization and wash temperatures. With some substrates, the temperature can be decreased by adding formamide to the prehybridization and hybridization solutions.

Hybridization can be performed at low stringency with buffers, such as 5×SSC with 1% sodium dodecyl sulfate (SDS) at 60° C., which permits complexes to form between two nucleic acid sequences that contain some mismatches. Subsequent washes are performed at higher stringency with buffers such as 0.2×SSC with 0.1% SDS at either 45° C. (medium stringency) or 68° C. (high stringency), to maintain hybridization of only those complexes that contain completely complementary sequences. Background signals can be reduced by the use of detergents such as SDS, Sarcosyl, or Triton X-100, and/or a blocking agent, such as salmon sperm DNA. Hybridization methods are described in detail in Ausubel (supra, units 2.8–2.11, 3.18–3.19 and 4–6–4.9) and Sambrook et al. (1989; *Molecular Cloning, A Laboratory Manual*, Cold Spring Harbor Press, Plainview N.Y.).

NSEQ can be extended utilizing a partial nucleotide sequence and employing various PCR-based methods known in the art to detect upstream sequences such as promoters and other regulatory elements. (See, e.g., Dieffenbach, C. W. and G. S. Dveksler (1995) *PCR Primer, a Laboratory Manual*, Cold Spring Harbor Press, Plainview N.Y.). Additionally, one may use an XL-PCR kit (PE Biosystems, Foster City, Calif.), nested primers, and commercially available cDNA (Life Technologies, Rockville Md.) or genomic libraries (Clontech, Palo Alto Calif.) to extend the sequence. For all PCR-based methods, primers may be designed using commercially available software, such as OLIGO 4.06 Primer Analysis software (National Biosciences, Plymouth Minn.) or another appropriate program, to be about 18 to 30 nucleotides in length, to have a GC content of about 50%, and to form a hybridization complex at temperatures of about 68° C. to 72° C.

In another aspect of the invention, NSEQ can be cloned in recombinant DNA molecules that direct the expression of PSEQ or structural or functional fragments thereof, in appropriate host cells. Due to the inherent degeneracy of the genetic code, other DNA sequences which encode substantially the same or a functionally equivalent amino acid sequence may be produced and used to express the polypeptide encoded by NSEQ. The nucleotide sequences of the present invention can be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In order to express a biologically active protein, NSEQ, or derivatives thereof, may be inserted into an appropriate expression vector, i.e., a vector which contains the necessary elements for transcriptional and translational control of the inserted coding sequence in a particular host. These elements include regulatory sequences, such as enhancers, constitutive and inducible promoters, and 5' and 3' untranslated regions. Methods which are well known to those skilled in the art may be used to construct such expression vectors. These methods include in vitro recombinant DNA techniques, synthetic techniques, and in vivo genetic recombination. (See, e.g., Sambrook, supra; and Ausubel, supra).

A variety of expression vector/host cell systems may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long term production of recombinant proteins in mammalian systems, stable expression in cell lines is preferred. For example, NSEQ can be transformed into cell lines using expression vectors which may contain viral origins of replication and/or endogenous expression elements and a selectable or visible marker gene on the same or on a separate vector. The invention is not to be limited by the vector or host cell employed.

In general, host cells that contain NSEQ and that express PSEQ may be identified by a variety of procedures known to those of skill in the art. These procedures include, but are not limited to, DNA—DNA or DNA-RNA hybridizations, PCR amplification, and protein bioassay or immunoassay techniques which include membrane, solution, or chip based technologies for the detection and/or quantification of nucleic acid or protein sequences. Immunological methods for detecting and measuring the expression of PSEQ using either specific polyclonal or monoclonal antibodies are known in the art. Examples of such techniques include enzyme-linked immunosorbent assays (ELISAs), radioimmunoassays (RIAs), and fluorescence activated cell sorting (FACS).

Host cells transformed with NSEQ may be cultured under conditions suitable for the expression and recovery of the protein from cell culture. The protein produced by a transgenic cell may be secreted or retained intracellularly depending on the sequence and/or the vector used. As will be understood by those of skill in the art, expression vectors containing NSEQ may be designed to contain signal sequences which direct secretion of the protein through a prokaryotic or eukaryotic cell membrane.

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Md.) and may be chosen to ensure the correct modification and processing of the expressed protein.

In another embodiment of the invention, natural, modified, or recombinant nucleic acid sequences are ligated to a heterologous sequence resulting in translation of a fusion protein containing heterologous protein moieties in any of the aforementioned host systems. Such heterologous protein moieties facilitate purification of fusion proteins using commercially available affinity matrices. Such moieties include, but are not limited to, glutathione S-transferase, maltose binding protein, thioredoxin, calmodulin binding peptide, 6-His, FLAG, c-myc, hemaglutinin, and monoclonal antibody epitopes.

In another embodiment, the nucleic acid sequences are synthesized, in whole or in part, using chemical or enzymatic methods well known in the art (Caruthers et al. (1980) Nucleic Acids Symp. Ser. 215–233; Ausubel, supra). For example, peptide synthesis can be performed using various solid-phase techniques (Roberge et al. (1995) Science 269:202–204), and machines such as the ABI 431A Peptide synthesizer (PE Biosystems) can be used to automate synthesis. If desired, the amino acid sequence may be altered during synthesis and/or combined with sequences from other proteins to produce a variant protein.

In another embodiment, the invention entails a substantially purified polypeptide (PSEQ) comprising the amino acid sequence of SEQ ID NO:8 or fragments thereof.

Screening, Diagnostics and Therapeutics

The polynucleotide sequences can be used in selection and evaluation of therapeutic molecules, diagnosis, prognosis, prevention, and treatment for diseases associated with hippocampus, such as Alzheimer's disease, Huntington's disease, schizophrenia, epilepsy, and their complications.

The polynucleotide sequences may be used to screen a library of molecules for specific binding affinity. The assay can be used to screen a library of DNA molecules, RNA molecules, PNAs, peptides, ribozymes, antibodies, agonists, antagonists, immunoglobulins, inhibitors, proteins including transcription factors, enhancers, repressors, and drugs and the like which regulate the activity of the polynucleotide sequence in the biological system. The assay involves providing a library of molecules, combining the polynucleotide sequence or a fragment thereof with the library of molecules under conditions suitable to allow specific binding, and detecting specific binding to identify at least one molecule which specifically binds the polynucleotide sequence.

Similarly the polypeptide or a portion thereof may be used to screen libraries of molecules in any of a variety of screening assays. The portion of the polypeptide employed in such screening may be free in solution, affixed to an abiotic or biotic substrate (e.g. borne on a cell surface), or located intracellularly. Specific binding between the polypeptide and molecule may be measured. The assay can be used to screen a library of DNA molecules, RNA molecules, PNAs, peptides, ribozymes, antibodies, agonists, antagonists, immunoglobulins, inhibitors, peptides, proteins, drugs and the like, which specifically bind the polypeptide. One method for high throughput screening using very small assay volumes and very small amounts of test compound is described in Burbaum et al. U.S. Pat. No. 5,876,946, incorporated herein by reference, which screens large numbers of molecules for enzyme inhibition or receptor binding.

In one preferred embodiment, the polynucleotide sequences are used for diagnostic purposes to determine the absence, presence, and excess gene expression. The polynucleotides may be at least 18 nucleotides long and consist of complementary RNA and DNA molecules, branched nucleic acids, and/or peptide nucleic acids (PNAs). In one alternative, the polynucleotides are used to detect and quantify gene expression in samples in which expression of NSEQ is correlated with disease. In another alternative, NSEQ can be used to detect genetic polymorphisms associated with a disease. These polymorphisms may be detected in the transcript cDNA.

The specificity of the probe is determined by whether it is made from a unique region, a regulatory region, or from a conserved motif. Both probe specificity and the stringency of diagnostic hybridization or amplification (maximal, high, intermediate, or low) will determine whether the probe identifies only naturally occurring, exactly complementary sequences, allelic variants, or related sequences. Probes designed to detect related sequences should preferably have at least 70% sequence identity to any of the nucleic acid sequences encoding PSEQ.

Methods for producing hybridization probes include the cloning of nucleic acid sequences into vectors for the production of mRNA probes. Such vectors are known in the art, are commercially available, and may be used to synthesize RNA probes in vitro by adding appropriate RNA polymerases and labeled nucleotides. Hybridization probes may incorporate nucleotides labeled by a variety of reporter groups including, but not limited to, radionuclides such as $^{32}P$ or $^{35}S$, enzymatic labels such as alkaline phosphatase coupled to the probe via avidin/biotin coupling systems, fluorescent labels, and the like. The labeled polynucleotide sequences may be used in Southern or northern analysis, dot blot, or other membrane-based technologies; in PCR technologies; and in microarrays utilizing samples from subjects to detect altered PSEQ expression.

NSEQ can be labeled by standard methods and added to a sample from a subject under conditions suitable for the formation and detection of hybridization complexes. After incubation the sample is washed, and the signal associated with hybrid complex formation is quantitated and compared with a standard value. Standard values are derived from any control sample, typically one that is free of the suspect disease. If the amount of signal in the subject sample is altered in comparison to the standard value, then the presence of altered levels of expression in the sample indicates the presence of the disease. Qualitative and quantitative methods for comparing the hybridization complexes formed in subject samples with previously established standards are well known in the art.

Such assays may also be used to evaluate the efficacy of a particular therapeutic treatment regimen in animal studies, in clinical trials, or to monitor the treatment of an individual subject. Once the presence of disease is established and a treatment protocol is initiated, hybridization or amplification assays can be repeated on a regular basis to determine if the level of expression in the subject begins to approximate that which is observed in a healthy subject. The results obtained from successive assays may be used to show the efficacy of treatment over a period ranging from several days to many years.

The polynucleotides may be used for the diagnosis of a variety of diseases associated with hippocampus. These include Alzheimer's disease, Huntington's disease, schizophrenia, and epilepsy.

The polynucleotides may also be used as targets in a microarray. The microarray can be used to monitor the expression patterns of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genome level.

In yet another alternative, polynucleotides may be used to generate hybridization probes useful in mapping the naturally occurring genomic sequence. Fluorescent in situ hybridization (FISH) may be correlated with other physical chromosome mapping techniques and genetic map data as described in Heinz-Ulrich et al. (In: Meyers, supra, pp. 965–968).

In another embodiment, antibodies or antibody fragments comprising an antigen binding site that specifically binds PSEQ may be used for the diagnosis of diseases characterized by the over-or-under expression of PSEQ. A variety of protocols for measuring PSEQ, including ELISAs, RIAs, and FACS, are well known in the art and provide a basis for diagnosing altered or abnormal levels of expression. Standard values for PSEQ expression are established by combining samples taken from healthy subjects, preferably human, with antibody to PSEQ under conditions suitable for complex formation The amount of complex formation may be quantitated by various methods, preferably by photometric means. Quantities of PSEQ expressed in disease samples are compared with standard values. Deviation between standard and subject values establishes the parameters for diagnosing or monitoring disease. Alternatively, one may use competitive drug screening assays in which neutralizing antibodies capable of binding PSEQ specifically compete with a test compound for binding the protein. Antibodies can be used to detect the presence of any peptide which shares one or more antigenic determinants with PSEQ. In one aspect, the anti-PSEQ antibodies of the present invention can be used for treatment or monitoring therapeutic treatment for diseases associated with hippocampus.

In another aspect, the NSEQ, or its complement, may be used therapeutically for the purpose of expressing mRNA and protein, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art can be used to construct vectors to express nucleic acid sequences or their complements. (See, e.g., Maulik et al. (1997) *Molecular Biotechnology, Therapeutic Applications and Strategies*, Wiley-Liss, New York N.Y.) Alternatively, NSEQ, or its complement, may be used for somatic cell or stem cell gene therapy. Vectors may be introduced in vivo, in vitro, and ex vivo. For ex vivo therapy, vectors are introduced into stem cells taken from the subject, and the transgenic cells are clonally propagated for autologous transplant back into that same subject. Delivery of NSEQ by transfection, liposome injections, or polycationic amino polymers may be achieved using methods which are well known in the art. (See, e.g., Goldman et al. (1997) Nature Biotechnology 15:462–466.) Additionally, endogenous NSEQ expression may be inactivated using homologous recombination methods which insert an inactive gene sequence into the coding region or other appropriate targeted region of NSEQ. (See, e.g. Thomas et al. (1987) Cell 51: 503–512.) Vectors containing NSEQ can be transformed into a cell or tissue to express a missing protein or to replace a nonfunctional protein. Similarly a vector constructed to express the complement of NSEQ can be transformed into a cell to downregulate the overexpression of PSEQ. Complementary or antisense sequences may consist of an oligonucleotide derived from the transcription initiation site; nucleotides between about positions −10 and +10 from the ATG are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. In: Huber, B. E. and B. I. Carr (1994) *Molecular and Immunologic Approaches*, Futura Publishing, Mt. Kisco N.Y., pp. 163–177.).

Ribozymes, enzymatic RNA molecules, may also be used to catalyze the cleavage of mRNA and decrease the levels of particular mRNAs, such as those comprising the polynucleotide sequences of the invention. (See, e.g. Rossi (1994) Current Biology 4: 469–471.) Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art and is described in Meyers (supra).

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

Further, an antagonist, or an antibody that binds specifically to PSEQ may be administered to a subject to treat or prevent a disease associated with hippocampus. The antagonist, antibody, or fragment may be used directly to inhibit the activity of the protein or indirectly to deliver a therapeutic agent to cells or tissues which express the PSEQ.

An immunoconjugate comprising a PSEQ binding site of the antibody or the antagonist and a therapeutic agent may be administered to a subject in need to treat or prevent disease. The therapeutic agent may be a cytotoxic agent selected from a group including, but not limited to, abrin, ricin, doxorubicin, daunorubicin, taxol, ethidium bromide, mitomycin, etoposide, tenoposide, vincristine, vinblastine, colchicine, dihydroxy anthracin dione, actinomycin D, diphteria toxin, Pseudomonas exotoxin A and 40, radioisotopes, and glucocorticoid.

Antibodies to PSEQ may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those which inhibit dimer formation, are especially preferred for therapeutic use. Monoclonal antibodies to PSEQ may be prepared using any technique which provides for the production of antibody molecules by continuous cell lines in culture. These include, but are not limited to, the hybridoma, the human B-cell hybridoma, and the EBV-hybridoma techniques. In addition, techniques developed for the production of chimeric antibodies can be used. (See, e.g., Pound J. D. (1998) *Immunochemical Protocols*, Methods Mol. Biol. Vol. 80). Alternatively, techniques described for the production of single chain antibodies may be employed. Antibody fragments which contain specific binding sites for PSEQ may also be generated. Various immunoassays may be used to identify antibodies having the desired specificity. Numerous protocols for competitive binding or immunoradiometric assays using either polyclonal or monoclonal antibodies with established specificities are well known in the art.

Yet further, an agonist of PSEQ may be administered to a subject to treat or prevent a disease associated with decreased expression, longevity or activity of PSEQ.

An additional aspect of the invention relates to the administration of a pharmaceutical or sterile composition, in conjunction with a pharmaceutically acceptable carrier, for any of the therapeutic applications discussed above. Such pharmaceutical compositions may consist of PSEQ or antibodies, mimetics, agonists, antagonists, or inhibitors of the polypeptide. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a subject alone, or in combination with other agents, drugs, or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton Pa.).

For any compound, the therapeutically effective dose can be estimated initially either in cell culture assays or in animal models such as mice, rats, rabbits, dogs, or pigs. An animal model may also be used to determine the appropriate concentration range and route of administration. Such information can then be used to determine useful doses and routes for administration in humans.

A therapeutically effective dose refers to that amount of active ingredient which ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to, mammals such as dogs, cats, cows, horses, rabbits, monkeys, and most preferably, humans.

EXAMPLES

It is to be understood that this invention is not limited to the particular devices, machines, materials and methods described. Although particular embodiments are described, equivalent embodiments may be used to practice the invention. The described embodiments are not intended to limit the scope of the invention which is limited only by the appended claims. The examples below are provided to illustrate the subject invention and are not included for the purpose of limiting the invention. For purposes of example, the preparation of the adult rat hippocampal cDNA library, RAHINOT01, is described.

I cDNA Library Construction

The rat hippocampus cDNA library, RAHINOT01, was constructed from hippocampal tissue removed from a pool of ten, male Sprague Dawley rats (Pharmakon, Waverly Pa.). The animals were housed in standard laboratory caging and fed PMI-certified Rodent Diet #5002 (Harlan Teklad, Madison Wis.). The animals appeared to be in good health at the time of tissue harvest. The animals were anesthetized by $CO_2$ inhalation and cardiocentesis was performed.

The frozen tissue was homogenized and lysed in TRIZOL reagent (1 g tissue/10 ml TRIZOL; Life Technologies), a monophasic solution of phenol and guanidine isothiocyanate, using a POLYTRON homogenizer (PT-3000; Brinkmann Instruments, Westbury N.Y.). Following homogenization, chloroform was added (1:5 v/v chloroform:homogenate), and the lysate was centrifuged. The aqueous layer was removed, and the RNA was precipitated with isopropanol. The RNA was resuspended in DEPC-treated water.

Messenger RNA (mRNA) was isolated using the OLIGOTEX kit (Qiagen, Valencia Calif.) and used to construct the cDNA library. The mRNA was handled according to the recommended protocols in the SUPERSCRIPT plasmid system (Life Technologies) which contains a NotI primer-adaptor designed to prime the first strand cDNA synthesis at the poly(A) tail of mRNAs. This primer-adaptor contains d(T) residues and restriction endonuclease recognition sites. Three loc-doc primers (Biosource International, Camarillo Calif.) were synthesized. Each had the same NotI-oligo d(T) primer-adaptor except for a single non-thymine base after the poly(T) segment. This introduced base served to reduce the length of the cloned poly(A) tail. These primers were purified using a SMART SYSTEM HPLC anion exchange column (MiniQ PC 3.2/3, Amersham Pharmacia Biotech, Piscataway N.J.) and then combined in an equimolar solution. After cDNA synthesis using SUPERSCRIPT reverse transcriptase (Life Technologies) and ligation with EcoRI adaptors, the product was digested with NotI (New England Biolabs, Beverly Mass.). The cDNAs were fractionated on a SEPHAROSE CL-4B column (Amersham Pharmacia Biotech), and those cDNAs exceeding 400 bp were ligated into the NotI and EcoRI sites of the pINCY 1 plasmid (Incyte Pharmaceuticals). The plasmid was transformed into competent DH5α cells (Life Technologies) or ELECTROMAX DH10B cells (Life Technologies).

II Isolation and Sequencing of cDNA Clones

DNA was isolated using the following protocol. Single bacterial colonies were transferred into individual wells of 384-well plates (Genetix Ltd, Christchurch UK) using sterile toothpicks. The wells contained 65 μl of sterile Terrific Broth (Life Technologies) with 25 mg/l carbenicillin and 0.4% glycerol (v/v). The plates were covered and placed in a Thermodyne incubator (Newtown Square Pa.) at 37° C. for 8–10 hours prior to use. Plasmid DNA was released from the cells and amplified using direct link PCR (Rao, V. B. (1994) Anal. Biochem. 216:1–14). The direct link PCR solution included 30 ml of Nucleix Plus PCR nucleotide mix (Amersham Pharmacia Biotech), 300 μl of Taq DNA polymerase (Amersham Pharmacia Biotech) and 6 μl Pfu DNA polymerase (Stratagene, La Jolla Calif.). Five microliters of PCR solution were added to each of the 384 wells using the HYDRA 96-well microdispenser system (Robbins Scientific, Sunnyvale Calif.). The plates were centrifuged at 1000 rpm for 20 seconds and refrigerated until use. A 384 pin tool (V&P Scientific, San Diego Calif.) was used to transfer bacterial cells from the incubation plate into the plate containing the PCR solution and 0.1% Tween 20 which lysed the cells and released the plasmid DNA. After lysis, the plates were covered with a cycle sealer, centrifuged up to 500 rpm, and cycled using a 384-well DNA ENGINE TETRAD thermal cycler (MJ Research, Watertown Mass.) using the program dPCR30 with the following parameters: Step 1) 95° C., 1 minute; Step 2) 94° C., 30 seconds; Step 3) 55° C., 30 seconds; Step 4) 72° C., 2 minutes; Step 5) steps 2, 3, and 4 repeated 29 times; Step 6) 72° C., 10 minutes; and Step 7) storage at 4° C.

The concentration of DNA in each well was determined by dispensing 100 μl PICOGREEN quantitation reagent (Molecular Probes, Eugene Oreg.) (0.25% reagent dissolved in 10 mM TrisHCl, pH 7.5, and 1 mM ethylenediamine tetraacetic acid (EDTA) (1× TE) v/v) and 0.5 μl of undiluted PCR product into each well of an opaque fluorimeter plate (Corning Costar, Acton Mass.) and allowing the DNA to bind to the reagent. The plate was scanned in a Fluoroskan II (Labsystems Oy, Helsinki, Finland) to measure the fluorescence of the sample and to quantify the concentration of DNA.

The cDNAs were prepared using either a MICROLAB 2200 system (Hamilton, Reno Nev.) or a HYDRA microdispenser (Robbins Scientific, Sunnyvale Calif.) in combination with the DNA ENGINE peltier thermal cyclers (MJ Research) and sequenced by the method of Sanger, F. and A. R. Coulson (1975; J. Mol. Biol. 94:441–448) using an ABI PRISM 377 sequencing system (PE Biosystems). Most of the isolates were sequenced according to standard ABI protocols and kits (PE Biosystems). The solution volumes were used at 0.25×–1.0× concentrations. In the alternative, cDNAs were sequenced using solutions and dyes from Amersham Pharmacia Biotech.

III Comparative Nucleic Acid Sequence Expression Analysis

Nucleic acid sequences, NSEQ, were first identified in rat tissue using electronic subtraction in ZOOSEQ 1.4 (Incyte Pharmaceuticals) to create a transcript image profile. Target tissue was adult rat hippocampus, and background tissue was fetal rat hippocampus. Transcript images for the two rat tissues were compared using the following settings: Stringency $\geq 50$; product score cutoff $\leq 100$; and maximum results displayed ALL. Rat clones which were present in the target tissue, but not in the background tissue, were recorded. In addition, rat clones which were present in the background tissue, but not in the target tissue, were recorded. The results included both annotated and unannotated clones. Unannotated clones and clones with annotation descriptions associated with hippocampal tissue were selected. Selected clones were clustered and then assembled using Phrap (P. Green, University of Seattle Wash.) or GCG Fragment assembly system (Genetics Computer Group, Seattle Wash.). The resulting rat contigs, SEQ ID NOs:9–15, were queried against LIFESEQ database (Incyte Pharmaceuticals) to identify homologous human nucleic acid sequences using BLAST with the following search parameters: Expected: 10; expected2: 0.15; Karlin and Atlschul sum statistics; and greedy spanning. Homologous human nucleic acid sequences were clustered and assembled using Phrap or GCG Fragment assembly systems as described above.

IV Homology Searching for Hippocampal Genes and Their Encoded Proteins

Polynucleotide sequences, SEQ ID NOs:1–7, and polypeptide sequence, SEQ ID NO:8, were queried against databases derived from sources such as GenBank and SwissProt. These databases, which contain previously identified and annotated sequences, were searched for regions of similarity using BLAST (Altschul, supra). BLAST searched for matches and reported only those that satisfied the probability thresholds of $10^{-25}$ or less for nucleotide sequences and $10^{-8}$ or less for polypeptide sequences.

The polypeptide sequence was also analyzed for known motif patterns using MOTIFS, SPSCAN, BLIMPS, and HMM-based protocols. MOTIFS (Genetics Computer Group) searches polypeptide sequences for patterns that match those defined in the Prosite Dictionary of Protein Sites and Patterns (Bairoch supra), and displays the patterns found and their corresponding literature abstracts. SPSCAN (Genetics Computer Group) searches for potential signal peptide sequences using a weighted matrix method (Nielsen et al. (1997) Prot. Eng. 10:1–6). Hits with a score of 5 or greater were considered. BLIMPS uses a weighted matrix analysis algorithm to search for sequence similarity between the polypeptide sequences and those contained in BLOCKS, a database consisting of short amino acid segments, or blocks of 3–60 amino acids in length, compiled from the PROSITE database (Henikoff; supra; Bairoch, supra), and those in PRINTS, a protein fingerprint database based on non-redundant sequences obtained from sources such as SwissProt, GenBank, PIR, and NRL-3D (Attwood et al. (1997) J. Chem. Inf. Comput. Sci. 37:417–424). For the purposes of the present invention, the BLIMPS searches reported matches with a cutoff score of 1000 or greater and a cutoff probability value of $1.0\times10^{-3}$. HMM-based protocols were based on a probabilistic approach and searched for consensus primary structures of gene families in the protein sequences (Eddy, supra; Sonnhammer, supra). More than 500 known protein families with cutoff scores ranging from 10 to 50 bits were selected for use in this invention.

VII Labeling of Probes and Hybridization Analyses

Polynucleotide sequences are isolated from a biological source and applied to a substrate suitable for standard nucleic acid hybridization protocols by one of the following methods. A mixture of target nucleic acids is fractionated by electrophoresis through an 0.7% agarose gel in 1× TAE [40 mM Tris acetate, 2 mM ethylenediamine tetraacetic acid (EDTA)] running buffer and transferred to a nylon membrane by capillary transfer using 20× saline sodium citrate (SSC). Alternatively, the target nucleic acids are individually ligated to a vector and inserted into bacterial host cells to form a library. Target nucleic acids are arranged on a substrate by one of the following methods. In the first method, bacterial cells containing individual clones are robotically picked and arranged on a nylon membrane. The membrane is placed on bacterial growth medium, LB agar containing carbenicillin, and incubated at 37° C. for 16 hours. Bacterial colonies are denatured, neutralized, and digested with proteinase K. Nylon membranes are exposed to UV irradiation in a STRATALINKER UV-crosslinker (Stratagene, La Jolla Calif.) to cross-link DNA to the membrane.

In the second method, target nucleic acids are amplified from bacterial vectors by thirty cycles of PCR using primers complementary to vector sequences flanking the insert. Amplified target nucleic acids are purified using SEPHACRYL-400 (Amersham Pharmacia Biotech). Purified target nucleic acids are robotically arrayed onto a glass microscope slide previously coated with 0.05% aminopropyl silane (Sigma-Aldrich, St. Louis Mo.) and cured at 110° C. The arrayed glass slide (microarray) is exposed to UV irradiation in a STRATALINKER UV-crosslinker (Stratagene).

cDNA probe sequences are made from mRNA templates. Five micrograms of mRNA is mixed with 1 µg random primer (Life Technologies), incubated at 70° C. for 10 minutes, and lyophilized. The lyophilized sample is resuspended in 50 µl of 1× first strand buffer (cDNA Synthesis system; Life Technologies) containing a dNTP mix, [$\alpha$-$^{32}$P] dCTP, dithiothreitol, and MMLV reverse transcriptase (Stratagene), and incubated at 42° C. for 1–2 hours. After incubation, the probe is diluted with 42 µl dH$_2$O, heated to 95° C. for 3 minutes, and cooled on ice. mRNA in the probe is removed by alkaline degradation. The probe is neutralized, and degraded mRNA and unincorporated nucleotides are removed using a PROBEQUANT G-50 Micro-Column (Amersham Pharmacia Biotech); Probes can be labeled with fluorescent nucleotides, Cy3-dCTP or Cy5-dCTP (Amersham Pharmacia Biotech) in place of the radio-labeled nucleotide, [$^{32}$P]dCTP.

Hybridization is carried out at 65° C. in a hybridization buffer containing 0.5 M sodium phosphate (pH 7.2), 7% SDS, and 1 mM EDTA. After the blot is incubated in hybridization buffer at 65° C. for at least 2 hours, the buffer is replaced with 10 ml of fresh buffer containing the probe sequences. After incubation at 65° C. for 18 hours, the hybridization buffer is removed, and the blot is washed sequentially under increasingly stringent conditions, up to 40 mM sodium phosphate, 1% SDS, 1 mM EDTA at 65° C.

To detect signal produced by a radiolabeled probe hybridized on a membrane, the blot is exposed to a PHOSPHORIMAGER cassette (Amersham Pharmacia Biotech), and the image is analyzed using IMAGEQUANT data analysis software (Amersham Pharmacia Biotech). To detect signals produced by a fluorescent probe hybridized on a microarray, the blot is examined by confocal laser microscopy, and images are collected and analyzed using GEMTOOLS gene expression analysis software (Incyte Pharmaceuticals).

VI Production of Specific Antibodies

SEQ ID NO:8, or portions thereof, substantially purified using polyacrylamide gel electrophoresis or other purification techniques, is used to immunize rabbits and to produce antibodies using standard protocols as described in Pound (supra).

Alternatively, the amino acid sequence is analyzed using LASERGENE software (DNASTAR, Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. Typically, oligopeptides 15 residues in length are synthesized using an ABI 431A Peptide synthesizer (PE Biosystems) using fmoc-chemistry and coupled to keyhole limpet hemacyanin (KLH; Sigma-Aldrich) by reaction with N-maleimidobenzoyl-N-hydroxysuccinimide ester (Ausubel supra) to increase immunogenicity. Rabbits are immunized with the oligopeptide-KLH complex in complete Freund's adjuvant. Resulting antisera are tested for antipeptide activity by, for example, binding the peptide to plastic, blocking with 1% BSA, reacting with rabbit antisera, washing, and reacting with radio-iodinated goat anti-rabbit IgG.

VII Screening Molecules for Specific Binding with the Nucleic Acid Sequence or Protein The polynucleotide sequences, or fragments thereof, or the polypeptide, or portions thereof, are labeled with $^{32}$P-dCTP, Cy3-dCTP, Cy5-dCTP (Amersham Pharmacia Biotech), or BIODIPY or FITC (Molecular Probes, Eugene Oreg.), respectively. Libraries of candidate molecules; e.g., DNA molecules, RNA molecules, PNAs, peptides, proteins, agonists, antagonists, antibodies, immunoglobulins, inhibitors, and drugs; previously arranged on a suitable substrate are incubated in the presence of labeled polynucleotide sequence or polypeptide. After incubation for a suitable period under appropriate conditions for the polynucleotide sequence or polypeptide, the substrate is washed, and any position on the substrate retaining label, which indicates specific binding or complex formation, is assayed, and the binding molecule is identified. Data obtained using different concentrations of the polynucleotide sequence or polypeptide are used to calculate affinity between the labeled polynucleotide sequence or polypeptide and the bound molecule.

What is claimed is:

1. A substantially purified polynucleotide comprising the polynucleotide of SEQ ID NO:7 or the completely complementary sequence thereof.

2. An expression vector comprising the polynucleotide of claim 1.

3. A host cell comprising the expression vector of claim 2.

4. A method for producing a protein, the method comprising the steps of:
   (a) culturing the host cell of claim 3 under conditions suitable for the expression of the protein; and
   (b) recovering the protein from the host cell culture.

5. A method of using a polynucleotide to screen a library of molecules to identify at least one molecule which specifically binds the polynucleotide, the method comprising:

(a) providing a library of molecules, (b) combining the polynucleotide of claim 1 with a library of molecules under conditions to allow specific binding, and (c) detecting specific binding, thereby identifying a molecule which specifically binds the polynucleotide.

6. The method of claim 5 wherein the library is selected from the group consisting of: DNA molecules, RNA molecules, PNAs, peptides, ribozymes, antibodies, agonists, antagonists, immunoglobulins, inhibitors, proteins including transcription factors, enhancers, repressors, and drugs.

* * * * *

SEQUENCE LISTING

```
<160> NUMBER OF SEQ ID NOS: 15

<210> SEQ ID NO: 1
<211> LENGTH: 1581
<212> TYPE: DNA
<213> ORGANISM: Homo sapiens
<220> FEATURE:
<221> NAME/KEY:
<223> OTHER INFORMATION: 239240
```

<300> PUBLICATION INFORMATION:

<400> SEQUENCE: 1

```
ggcggaggag gcgccgcggc ggagccccgg acgcgaccat gtcggaggtg ctgccctacg      60
gcgacgagaa gctgagcccc tacggcgacg gcggcgacgt gggccagatc ttctcctgcc     120
gcctgcagga caccaacaac ttcttcggcg ccgggcagaa caagcggccg cccaagctgg     180
gccagatcgg ccggagcaag cgggttgtta ttgaagatga taggattgat gacgtgctga     240
aaaatatgac cgacaaggca cctcctggtg tctaactccc ccaaagacaa tgagttaagg     300
gagagaataa gaacggcggt aacagttatt ggcaaaaagc atgaaaagag aaagcacttt     360
gaaatttatt actagcttgc tacccacgat gaaatcaaca acctgtatct ggtatcaggc     420
cgggagacag atgaggcgag aggaggagga ggaggaggag aaggctctgg gctcctctgc     480
aaaaataaaa ataaaaaaat aaataaaatt ttaaaaataa taaaaattca ctatatacac     540
atataaagaa ataaaaagaa gtctcagttg cagctatttg tcaaaattaa tatccatttc     600
tttttatata cggtgaatat tgcgcaatta tagatctgga ttttgaacca cttaatgaag     660
cggcaacacc aggtgttttg aggtgttggc attcttcgct gatttggctg ttcccaatgt     720
ttacattatt taatcttgca aaaatggttc tgtgcacttg gatgtgaaat gctgtccagt     780
tttatttttt ttatgttgtt atccttggat gtacaaaaaa ttcagaaaat gatctctgta     840
gatattctgt tttatttttgg tcatctttag aagttatcag gaatgtgttt aaaacaagaa     900
gagaactttt ctaaggaatg atacatagaa aagatttttat tttaaaatga gttgtaaagc     960
ttgtgtttct ttgttgctgc aagctatctg cccaagttaa tgcaaatgga cacattttt     1020
atgtcagaaa aacacacaca cacacacaca cacacacaca cacacacaca cacacacgaa    1080
aaacaaagaa aaaatgctt gagcttttc taacttcccc ttgcagtctg ttgtgtgagc      1140
agcctgttta tttctctaat attatgtcag tttattctct ttaatggact gtaaaaaat     1200
gtaatcacaa gagtgccaaa tatcttgaaa tgccaaaagg catttttagtt tcttttctct    1260
gtgctctgag tccacgtaca ggaatgcttg gagtgtcttt tctgttattt ataggggatc     1320
tcttaaggca caccagctgc ctgttttgca tggtatttgc aaaaatgcct cttgcgtgag     1380
gaaatctttt accattttt gtttgcaact ttggacctca agaggtttcc cttcccttcc      1440
ccgttccctc tttctttaat tcaatattct gtatgttgca ccttgaacca gcacacaggg     1500
ctatttctcc aatgtacaat aaaagaattg ttcctgtgtc tcaaaaaaaa aaaaaaaaa     1560
aaaaaaaaa aaaaaaaaa a                                                1581
```

<210> SEQ ID NO: 2
<211> LENGTH: 1910
<212> TYPE: DNA
<213> ORGANISM: Homo sapiens
<220> FEATURE:
<221> NAME/KEY:
<223> OTHER INFORMATION: 350293
<300> PUBLICATION INFORMATION:

<400> SEQUENCE: 2

```
agcagcaggt gcctaagtcc tccctggcac tggcaggcct tacctcacat tgctaaatta      60
aagcaatgca attcctcttg ggtaagagga attcctcctt ctttactaac tgatccccag     120
caaggaaata aaatgttagg ctttaaaaat ccctactttg tcatatcaga ctatattcta     180
aaactatatt tgagcgaaac ctgtcattgc gtctaatttc aaatatacag aatctcctta     240
agagctgttg ccttattttt ttgtaaagcc tctctgacat caaatgggga gaaatggtgg     300
```

```
cacctccaga caccctgaaa ctacacacca tttcttccct gctcagcttc tgctcaggag    360
ttctgtgagc tatgggaagg ccattggttg tatttgctac ttttactttc atcttcctct    420
gctgtagagc catttaatgt tattgtcata tgctgctggt gaggtaaagg tgggtccggg    480
tgccttccca ggggttagag gatgttcaaa gggccgattt cagcaggagt tcagagggct    540
tatgatgaat ggtgagagat ttgacaacca ccagagcaca tgtgctctga ccctctcctg    600
ggcattggtt cctgctggta ccgggcggtt cagaccttca ataggttgc tttcaaaaga     660 gctttcaggc acttattgag aattaatgtt taaacagaca taatagccta gatgaactcc    720
caagagatct attaaatctt gtgggctgaa taaatatctc gtgcaggact gtgcaacagt    780
tagcccagag catcctgcct gtgggcatcc acctcccagg tgagggcagt gggaagctgg    840
cccgacggca gccagaactt gtttctcacc tcccaccagc aacccccac ccaactctgg     900 gccccaggca cacgaagcac aagtctcagg ggaccattcc cacattgggg gatcctgagg    960
gagcccatca ccgcctcttg catacaactg tccactagga ggcacgccca gtgtgggaga    1020
gatgtatggt cttgccttcc acctgtaaaa actgcacata tgcaagccat ttgcactctg    1080
gaactgcatg ccgtgaaaac tcctaatggt gtggaactta gtttgaattt gaaatcacgc    1140
cgcatgcaca aagggacagg cccaggcccg acctcaggtc atccgcccgc tggctgcaga    1200
gcatccctgg gagccaaggc gaggcccgtg gagcctgagc tttgtgtagc tcgagctttg    1260
tgtagctcgt gcacttatta tgcaccacct cccttcagtc accactcctc ttcctccgcc    1320
atcctcattt atactgattg cacacccccc gctcaaacaa caatgtcctt attatgatga    1380
ccatctcgta gtggtacatt ccattcctat ttaaggtaag cccaaagccc acttttggat    1440
tttctcgact gtccgagaaa agttgtgtaa gcgcctgcgt tcttctgggt ttggctagat    1500
agggttgtgt ccctctatgg aatggagagt gatgtgggca agggtgtcat tttctcgcac    1560
aatacaactc actgaggatg cttctgtaga agtgagaaac acgatgagta cattcagaat    1620
tacaataact cactctcact gggtaacttc tcatgataga tttgtatgat caatacgggt    1680 ctattttat gtcaactgaa cactgtaggg taccttccag tcttttttcaa gattgttaaa    1740 ttgagacaag taattgaata atttgtccta ttttttatttt aaaaaagtg aatggactga    1800 aatgttaaat gtgaatgtac atttcttaat tgcaactttt ctactgagtg tttgcactat    1860
actttctgga atcttatttta acaaaaataa agggaaaaaa ttgcttgact               1910
```

<210> SEQ ID NO: 3
<211> LENGTH: 1942
<212> TYPE: DNA
<213> ORGANISM: Homo sapiens
<220> FEATURE:
<221> NAME/KEY: unsure
<222> LOCATION: 357, 514, 515, 545, 547, (554)...(582)
<223> OTHER INFORMATION: a or g or c or t, unknown, or other
<220> FEATURE:
<221> NAME/KEY:
<223> OTHER INFORMATION: 244771
<300> PUBLICATION INFORMATION:

<400> SEQUENCE: 3

```
cgtcaccgcc acttgccgca tccgcaagat ctctctggac cagctcgggt gcagggcctc      60
tgcgggaagc cctcctagac ctctgcggct tctcctctaa catggccgac tcggaaaacc     120
aggggcctgc ggagcctagg ccaggcgcg cagcggcgg aggcagcggc agaggaggta       180
atggcggaag gcggtgcgca gggtggagac tgtgacagcg cggctggtga ccctgacagc     240
```

-continued

| | |
|---|---|
| gcggctggtc agatggctga ggagcccag acccctgcag agaatgcccc aaagccgaaa | 300 |
| aatgacttta tcgagagcct gcctaattcg gtgaaatgcc gagtctggcc ctcaaanagc | 360 |
| tgcagaagcg atgcgataag atagaagcca aatttgataa ggaatttcag gctctggaaa | 420 |
| aaaagtataa tgacatctat aagcccctac tcgccaagat ccaagagctc accggcgaga | 480 |
| tggagggggtg tgcatggacc ttggagggggg aggnngagga ggaagagaag tacgaggatg | 540 |
| acgangngga gggnnnnnnn nnnnnnnnnn nnnnnnnnnn nncagaggct gccgcggggg | 600 |
| ccaaacatga cgatgcccac gccgagatgc ctgatgacgc caagaagtaa gggggggcaga | 660 |
| gatggatgaa gagaaagccc acgaagaaaa aagcctggtt ttgttttttcc cagaatatcg | 720 |
| atggacttaa aaaggctcag gttttttgacc aaaatacaat gtgaatttat tctgacattc | 780 |
| ctaaaataga ttaaattaaa gcaattagat cctggccagc tcgattcaaa tttgactttc | 840 |
| attttgaaca taataaatat atcaaaaggt gttaaagaaa actgaattaa acccaaaatt | 900 |
| atgtttttcat ggtctcttct ctgaggattg aggtttacaa agggtgttag cagatgcgaa | 960 |
| gtaaagaacg tcactttgaa acccattcat cacacagcat acgctacaca tggaacaccc | 1020 |
| aagccatgac tgaacacgtt ctcagtgctt aattcttaaa tttctttact catgacattt | 1080 |
| cggcagtgca gagaaggcag aacccaagaa aaacgtcatc tttgagactt tgcttttgta | 1140 |
| acgcagacat cagctttaca cttcacagga gattgatggc attgaggaag attgcaatgg | 1200 |
| agatcatgac actactgtta ataaggccag gaaaactgcc atttcaagtt ctgaaaaatg | 1260 |
| ttttgagtat ttgaatttag agaaacaaca tggttccaag aaggagggtg taaaacctgt | 1320 |
| aaaatactgt caacatatgt attcattagt tacaatctca tgtttgtgtt ttcttagtac | 1380 |
| tgtctattta caaacacgta aaaaatacc caaatatgtt taagtattaa atcactttac | 1440 |
| ctagcgtttt agaaatatta atttacttga agagatgtag aatgtagcaa attatgtaaa | 1500 |
| gcatgtgtat ccagcgttat gtactttgcg ccttgtgacg tctttctgtc atgtagcttt | 1560 |
| tagggtgtag ctgtgaaaat catcagaact cttcactgaa gctaatgttt ggaaaaaata | 1620 |
| tatacttgaa gaaccaatcc aagtgtgtgc ccctaccccc agctcagaag tagaaagggt | 1680 |
| ttaagtttgc ttgtattagc tgtgccttca ttattttgct atgtaaatgt gacatattaa | 1740 |
| ttataaaatg gtgcataatc aaattttact gcttgaggac agatgcatac agtaaggatt | 1800 |
| tttaggaaga atatatttaa tgtaaagact cttagcttct gtgtgggttt tgaattatgt | 1860 |
| gtgagccagt gatctataaa gaaacataag cttaaagttg tttatcactg tggtgttaat | 1920 |
| aaaacagtat tttcaaaaaa ta | 1942 |

<210> SEQ ID NO: 4
<211> LENGTH: 1544
<212> TYPE: DNA
<213> ORGANISM: Homo sapiens
<220> FEATURE:
<221> NAME/KEY:
<223> OTHER INFORMATION: 5308642
<300> PUBLICATION INFORMATION:

<400> SEQUENCE: 4

| | |
|---|---|
| gatttctatt actagttttt ctaagctatt tacagagtgt tgtagctttt catttgcagc | 60 |
| attatgttcc cacaaattct gtactcagca tatacagtat agtttatctg ctctatttct | 120 |
| gtcttataga aatcatgaat gtggtctgca gacattgatg aagaaaatct gttggtaatt | 180 |
| gatacatggg ctaaagcatc agaggtttaa tttgaagttt atgttcacac actgaaaact | 240 |
| tagtttttttt gttggtagat ccatgtgcat gctagaattt gggacaggca ctatttgcat | 300 |

```
aaagtattaa agtcaatttt taaactaagc aaaggtacac gttgtaacgg tggggcatct      360
gtgaaaaga tgtcccttc ataatatatg caatatattc cagatgtttt gagagattac      420
agaagaggag gcctgcttca cttgcagata agtttattat aattctccag aaatgtgcag      480
gatgtgcatt agcaaattgc actgtacttt tcactccagc ctgggtgaca gagcaagact      540
cccgtctcgg gggcttaaaa aaaaaaaat gctgtatcta aatgaatctg tgtaattggg      600
cccagatgtg ggtttgctca gtattagtag acaaggtctt tgttcagacg attaggtgcc      660
taactggcaa atgccttagt ttcttaaaac gtattttctg atgtggcttt acatttcaaa      720
agtgaacttg attcaacctg agaaaactga ttaaaaaatt agtttaaatt tgccagcagg      780
gaagtaaaat aattatggga agagtgtctt aagcctaata ttaaatcagt tttgttaagg      840
ggaaaactca atagttctgt tacttaggct gttagatcca agttgatttt tgtgtctaca      900
gctaaatttt gtttacaatt aggctatttt ttaatatagg atttagaaac caagggtatg      960
tgttttaaaa ttacactttt tcttaacctg tctagctgtc ggaaaaggta acagaagatg     1020
gaactcgaaa tcccaatgaa aaacctaccc agcaaagaag catagctttt agctctaata     1080
attctgtagc aaagccaata caaaaatcag ctaaagctgc cacagaagag gcatcttcaa     1140
gatcaccaaa aatagatcag aaaaaaagtc catatggact gtggatacct atctaaaaga     1200
agaaaactga tggctaagtt tgcatgaaaa ctgcactta ttgcaagtta gtgtttctag     1260
cattatccca tcccttgag ccattcaggg gtacttgtgc atttaaaac caacacaaaa     1320
agatgtaaat acttaacact caaatattaa cattttaggt ttctcttgca gatatgagag     1380
atagcacaga tggaccaaag gttatgcaca ggtgggagtc ttttgtatat agttgtaaat     1440
attgtcttgg ttatgtaaaa atgaaatttt ttagacacag taattgaact gtattcctgt     1500
tttgtatatt taataaattt cttgttttca aaaaaaaaaa aaaa                    1544
```

<210> SEQ ID NO: 5
<211> LENGTH: 893
<212> TYPE: DNA
<213> ORGANISM: Homo sapiens
<220> FEATURE:
<221> NAME/KEY: unsure
<222> LOCATION: 367
<223> OTHER INFORMATION: a or g or c or t, unknown, or other
<220> FEATURE:
<221> NAME/KEY:
<223> OTHER INFORMATION: 2289256
<300> PUBLICATION INFORMATION:

<400> SEQUENCE: 5

```
ataaaaaatg ggaagaaatg taaaaggaa gaaaggaaga gaggtaatat attaaggaat       60
aaatacatgc atgcagattt aagacagagc catgctagaa caggaatgaa aggctgtgtg      120
aaccaagcag accgcttaat tggcaccagt gctgctggta tggtcaatca cctactcaac      180
taaggaacgg ctcaaagcat acacatggga gggaggagtg gggccacaga gagggccc       240
attagttgca gattacgatg tatccagtta ggtgcacctg ccttcgagaa gtgtaaaaat      300
aagtatttac atagaaagaa agactgaatg gatgcacggt gaatgcatga atgattgaac      360
gacaganaag atttgcattg accgatgagg agggcattgt agacagggat gagggtcatt      420
gatcctgggt gcagatctcc aaaaggattg ccagaaggaa ggagggagtg gtggaaagaa      480
acaataggtt gggaaaaaat gaaaatagga aaaaggaag tgaaagagat aataaataat      540
tagatcaaat aagttgatga aaggggactg gtttagcaca agccatccac attaattcaa      600
```

| acctgtggct ctgaagtttg ttttttaaat gaccacaagt gtaagactga atgaaagaat | 660 |
| aaatgcgtgc attccatagg atgcaagaaa aggagtgagg aatgggaaaa ttggaagaac | 720 |
| gagaggggga gagatgtaag aaaagaaagg aaaagtgaag taggcatatg aaagaaaagg | 780 |
| cacttcttgg acaagcactg aaatataatg agacagtttt acccattaaa tataataaac | 840 |
| agtaaacgtt gaggttcatc aataaaagca cagatacctg aatagaggag tga | 893 |

<210> SEQ ID NO: 6
<211> LENGTH: 703
<212> TYPE: DNA
<213> ORGANISM: Homo sapiens
<220> FEATURE:
<221> NAME/KEY:
<223> OTHER INFORMATION: 1941247
<300> PUBLICATION INFORMATION:

<400> SEQUENCE: 6

| agcggccgcc cttttttttt tttttttttt tttttttttt tttttttttt tttttttttt | 60 |
| ttttttttga gagttgaaaa caagattgac gtaacccttt attgcaaatt ctaaagtaaa | 120 |
| aagatgtaca gtacaaagta aaattgaaat ttcatactat aaacttccaa tccacttaca | 180 |
| cattctcatt tctcaagcat ttctgccatt tccgcataaa cagaacaggg aacaagtcga | 240 |
| ggaggtgagg aaggagata cagcaagggg aaaaaattgt cttgaataat cacaaacccc | 300 |
| agaagcaagt gaaaggaaag cattttctc gacctgctgt cctggtgatg agaagcgggg | 360 |
| gtggttggag cagtgcagtt taaatggct ctcagaatag cagcatttat ggtaccattt | 420 |
| cagcttcctt aagtccaata atactttgcc cttccctagc gcctttgcct ctgtatctca | 480 |
| aaacgcttta caaacatttt agttaaagcc tcacaacacc cctgtgaggt aggtcagtat | 540 |
| tattatcccc attttacaga tggggaaact gaggcacaga gaggttaagt gacttgccca | 600 |
| aggccacaca gcgagccagc ggtcaagcta ggggacagac acagtctgg tccttttct | 660 |
| ggaaccactg gaccacactc cccttaacc tatatacatt ctt | 703 |

<210> SEQ ID NO: 7
<211> LENGTH: 829
<212> TYPE: DNA
<213> ORGANISM: Homo sapiens
<220> FEATURE:
<221> NAME/KEY:
<223> OTHER INFORMATION: 3864594
<300> PUBLICATION INFORMATION:

<400> SEQUENCE: 7

| ccaggcacct gacgcctctt tcccctcacg gtgccagggc cgggccgaac tacatttccc | 60 |
| aggaggctcc gcggccaggt gcaaacagcg ccgtgctgac tacatttccc agacagcctt | 120 |
| gcggcggccc gggccttaaa gcgtccattt cccagcggcc ctccgctgcg agaccgcagc | 180 |
| ccttctctgg agtctcagag ccgcaagaca ccacgactcc cagaggacct tgcgtcgggc | 240 |
| aagaaagact acaccttcca gaggcctctg cggcgccgcg acaggaagcg gcgggcgagc | 300 |
| cgagtgtcct tgcgcgtgga tccgagcgac catggtggcc cgggtgtggt cgctgatgag | 360 |
| gttcctcatc aagggaagtg tggctggggg cgccgtctac ctggtgtacg accaggagct | 420 |
| gctggggccc agcgacaaga gccaggcagc cctacagaag gctggggagg tggtcccccc | 480 |
| cgccatgtac cagttcagcc agtacgtgtg tcagcagaca ggcctgcaga taccccagct | 540 |
| cccagcccct ccaaagattt actttcccat ccgtgactcc tggaatgcag gcatcatgac | 600 |
| ggtgatgtca gctctgtcgg tggccccctc caaggcccgc gagtactcca aggagggctg | 660 |

-continued

```
ggagtatgtg aaggcgcgca ccaagtagcg agtcagcagg ggccgcctgc cccggccaga      720
acgggcaggg ctgccactga cctgaagact ccggactggg accccactcc gagggcagct      780
cccggccttg ccggcccaat aaaggacttc agaagtgtaa aaaaaaaaa                  829
```

<210> SEQ ID NO: 8
<211> LENGTH: 118
<212> TYPE: PRT
<213> ORGANISM: Homo sapiens
<220> FEATURE:
<221> NAME/KEY:
<223> OTHER INFORMATION: 3864594
<300> PUBLICATION INFORMATION:

<400> SEQUENCE: 8

```
Met Val Ala Arg Val Trp Ser Leu Met Arg Phe Leu Ile Lys Gly
  1               5                  10                  15

Ser Val Ala Gly Gly Ala Val Tyr Leu Val Tyr Asp Gln Glu Leu
                 20                  25                  30

Leu Gly Pro Ser Asp Lys Ser Gln Ala Ala Leu Gln Lys Ala Gly
                 35                  40                  45

Glu Val Val Pro Pro Ala Met Tyr Gln Phe Ser Gln Tyr Val Cys
                 50                  55                  60

Gln Gln Thr Gly Leu Gln Ile Pro Gln Leu Pro Ala Pro Pro Lys
 65                  70                  75

Ile Tyr Phe Pro Ile Arg Asp Ser Trp Asn Ala Gly Ile Met Thr
                 80                  85                  90

Val Met Ser Ala Leu Ser Val Ala Pro Ser Lys Ala Arg Glu Tyr
                 95                 100                 105

Ser Lys Glu Gly Trp Glu Tyr Val Lys Ala Arg Thr Lys
                110                 115
```

<210> SEQ ID NO: 9
<211> LENGTH: 1045
<212> TYPE: DNA
<213> ORGANISM: Rattus norvegicus
<220> FEATURE:
<221> NAME/KEY: unsure
<222> LOCATION: (871)...(899)
<223> OTHER INFORMATION: a or g or c or t, unknown, or other
<220> FEATURE:
<221> NAME/KEY:
<223> OTHER INFORMATION: 700122146
<300> PUBLICATION INFORMATION:

<400> SEQUENCE: 9

```
aataaaataa aaaataaaaa tcactatata cacacatata aaagaaaaaa gtgtcagttg       60
cagctacttg tcgaaattaa tacctgtttc tttttatcta tggtaaatat cgtgcaatta      120
tagatctgga ttttgaacca cttcctgaaa gcagcaccag agtactcgaa ggtgcttgtg      180
ttctctgctg atttggctgt ttccaatgtt tacattattt aatcttgcaa aaatgatcct      240
gtgcacttgg atgtgacatg ctgtctagtc cggtttcatc ttttttttta atgttgttta      300
tttttggatg tacaaaagaa aaattggggg gagggggtga tctctgtaga tactcttgta      360
ctttgaagtt accggaaatg gaacgggtct taaagcagaa agtaactttt ccaaggaaca      420
gatgcttgcg aaggccccct tccttgtctt attctccaga gacaactgaa atttagcttc      480
tttgttgcag caaagctctt tgcccaggtg aacactgacc accgcgggtt ttctatgtca      540
gaaagaagaa gaaaacaaaa acatgctcga gctttttcta acctccccctt ggggtctgt      600
```

-continued

```
tgtgcgaacc cctctttctt caatatcgtg tcactttatt ctctttaatg gactgtaaca      660
aacaacaaca acaatgtaat cacgagagtg ccaaatatct tgaaacgcca aaaggcattt      720
tggtttcctt ttctcccctg tgctctgagt cttcgtactg gaacgcttgg agtgtctttt      780
ctgttattta tagggttct cttaaggctc tcgccagctg cctgttttgc atggtatttg       840
caaaaaaaaa aatgcctctt gcgtgaggaa nnnnnnnnnn nnnnnnnnnn nnnnnnnnng      900
caactttgga cctcaagagg tccccacccc agtcccagtt ccttcttttc ttaattcttt      960
attctgtatg ctgcaccttg aaccagcaca cagggctatt tctccaatgt acaataaaga     1020
acttccatgt gtctcctttc aaaaa                                           1045
```

<210> SEQ ID NO: 10
<211> LENGTH: 1238
<212> TYPE: DNA
<213> ORGANISM: Rattus norvegicus
<220> FEATURE:
<221> NAME/KEY: unsure
<222> LOCATION: (786)...(810)
<223> OTHER INFORMATION: a or g or c or t, unknown, or other
<220> FEATURE:
<221> NAME/KEY:
<223> OTHER INFORMATION: 700244771
<300> PUBLICATION INFORMATION:

<400> SEQUENCE: 10

```
cccaaacctt tccagccact tgctgagaat cagcatttct acagagatgc gctctgagac       60
tgactccaga aatctcttag acttcataag catgtaggat ggcctgcaag aacatttgca      120
ggccactaga tctgcctggg gaggggtgg tgtcccctg ctccattaca ctgcaatggg        180
aagtgggcct gacagcagcc agaacttgtt tctcacctcc caccagcaac ctccactcag      240
tcccaaaccc caggcacatg aagcacaagt ctcagggac cgttcccatg ctgtggggag       300
cccaaggaag cccccagcat ctcttgcata caccactggc agtgtgggca caactggcca     360
ccaggagcac acatgtctgg ggaggagggg cctgctctgt tgccttcacc cctgttaaaa     420
ttgagtatat gcaagccatt tgcactatgg aattgcatgc catgaaattc ctaattgtgt      480
gcaccttagt ttgaatttga cactatgtag catgcacaaa agaatggaag ggcttgggct      540
tgtccccaag tcacctctcc tgctcattgg gagcacaacg tcaccctcag ccaatcccag      600
gttttgtgga gctggtgtgg ctccagcact taactgtcca gtgtctccct ccccaccat       660 gctcccactt cagctgaatg ctcaccagtt tccacaaacg gaaatgtcgt tatggtcact      720
gtcttggcag taattctatc tggatttgaa gtaagcccaa agccctcttc tggagtttct      780
tacttnnnnn nnnnnnnnnn nnnnnnnnnn ggcatgtacg cacctgtgtc ctgtgtttat      840
ccaagaaagc tttgagtccc ttagcgggtg cacggacaaa gggggcact ttatcccaca       900 tgataaactt accagatgtg tccgtagcta tgagaactca atgatcatat tcacaataac      960
tcaatatcac tgggtaacct ctcacaatag atttgtataa ccaatacggg tctattttta     1020
tgtcaactct gtggagcgcc ttccagtctt tttcaaggtt gttaaaatcg agacgagtaa     1080
ttgaataatt tgtcctattt ttatttaaaa agtgaatgga ctgaaatgtt aatgtgaatg     1140
tacatttctt aactgcaact tttctactga gtgtttgcac tatactctct ggggtcttat     1200
ttaacaaaaa taaggagaa aaattgcttg actaaaaa                             1238
```

<210> SEQ ID NO: 11
<211> LENGTH: 1141
<212> TYPE: DNA
<213> ORGANISM: Rattus norvegicus
<220> FEATURE:

<221> NAME/KEY: unsure
<222> LOCATION: 2, 13, 35, 38, 39, 41, 42, 43, 47, 1069, 1073, 1074
<221> NAME/KEY: unsure
<222> LOCATION: (1076)...(1080), 1082, 1083, 1086, 1087, 1089, 1095
<221> NAME/KEY: unsure
<222> LOCATION: 1097, 1098, 1100, 1103, 1106, 1110, 1114, 1115, 1122
<221> NAME/KEY: unsure
<222> LOCATION: 1126, 1128, 1130, 1131, 1133, 1140
<223> OTHER INFORMATION: a or g or c or t, unknown, or other
<220> FEATURE:
<221> NAME/KEY:
<223> OTHER INFORMATION: 700244870
<300> PUBLICATION INFORMATION:

<400> SEQUENCE: 11

| | | | | | |
|---|---|---|---|---|---|
| gnttgggttt | ttntaacggc | ctaattaaac | gtatnggnng | nnntggnggg | cttctgtgag | 60 |
| aaccagactt | gagactgatg | aaaggttgtc | agttagatgg | gaattaaagt | gcgtcacacg | 120 |
| ttgaaatcca | ttcatcacac | tacaccttaa | cacccaagct | aagacagaac | tcttctcaat | 180 |
| gcttaattct | tcagtttctt | tacatttccc | agcgcagagg | aagaggaacc | caagaacgac | 240 |
| gtcatctttta | agacttttgc | ttttgcaaac | ccagacatca | gctttacact | ccagaggaga | 300 |
| caaggcatgg | aggaaggctg | gactgacagc | atttactgtt | tatgtggcta | gaaaaactgc | 360 |
| catttcaagt | tgtgaaaaat | gttttgaata | tttgaattta | cagaaagaac | acggttccaa | 420 |
| aaataagggt | gtattccatg | tataatattg | tcaacacgtg | ttcatctgta | atggtctcat | 480 |
| gttatctgtt | ttcttggtag | tgtttgttta | caaaatcgta | aaaattaccc | caaatgttttt | 540 |
| aagtattaaa | ttcccttata | gcattttaga | aatataattt | acttgaagag | atgtagaatg | 600 |
| tagcaattct | gtaaagccat | gtgtatccag | tgttgcctag | tttgacttgt | gaagtctttt | 660 |
| gtctgtagct | ttagcaagta | gcgtgaaaac | catcagaact | cctcaatgaa | gctaatgttt | 720 |
| ggaaaaaagt | atatacttga | agaaccaacc | caagtgtgta | tccccaaccc | cagctcagaa | 780 |
| ataggaagga | tttaagtttg | cttgtattag | ctgtgccttc | attattttgc | tatgtaaatg | 840 |
| tgacttatta | aatggtgcat | aatcaaattt | tattgcttga | ggacaaaaat | ggcataaagg | 900 |
| gaagactttt | gggaaaagac | atttaatgta | aagcctttag | cttctttgtg | ggttttgaac | 960 |
| tatctgtgaa | tcaatgttct | gtaaagaaac | acaaacgtaa | agttgtttac | cactgtggtg | 1020 |
| ttaacaaaac | agtattttca | aaaataaaaa | aaacttgtta | ttctgaaana | aannannnnn | 1080 |
| tnnaannana | tttgngnntn | atngaaaan | ttanngagag | anggtntntn | ngngggctn | 1140 |
| g | | | | | | 1141 |

<210> SEQ ID NO: 12
<211> LENGTH: 1573
<212> TYPE: DNA
<213> ORGANISM: Rattus norvegicus
<220> FEATURE:
<221> NAME/KEY:
<223> OTHER INFORMATION: 700025020
<300> PUBLICATION INFORMATION:

<400> SEQUENCE: 12

| | | | | | |
|---|---|---|---|---|---|
| gtacaccatt | atgttcccaa | aagtctgtgc | tcagcataca | gtatagttta | tctgctttat | 60 |
| ttctgtctta | tagaaatcat | gaatgtggtc | tccagacaat | gatgaagaaa | atctgttggt | 120 |
| aattgatcat | gggttcaagt | gtcagaattt | acgtttacag | aataaagctt | agtctttgtt | 180 |
| gaaggtagtc | catgtgcatg | ctagagttttt | gggctaggga | ctatgtgtgt | aaggcagttt | 240 |
| gacagctcag | cctagaagca | ctgtcatggt | ggggcatcgg | tgaattagac | atccctcaca | 300 |
| taatatatgc | aatatattcc | agatgttttg | agagattaca | gaagaagagg | cctggcttca | 360 |

```
cttgcagata agtttattac aattctccag aactacagag gatgtgcact ggcacctcgc      420
attgtattta taggttaatt tttcatgtgt gaaaccttga tcttaagatt ttgggctggg      480
atgtaactca gtttgtagag agcctgtcga gggtgcagta acactggggg ttagttccca      540
gcactgataa ctgggtttag tacccccatac ctgtgatccc cagcagttgg gagactgtcc    600
ttggacagct agggagataga tacaagagat gtggtctcag aaaaccactt tatagaaatg    660
taaggttaaa aagataacag aataatggag atagtttgtc tgttgctgag atctcagggg    720
ctgtatagtg tttgctcagg caagtgccca agaggggcgc cttgatgaat gaattacaaa    780
tgcttcagtt ctttgacaaa cattttttat tgtacttact cagaatgagt tgtatctaca    840
acaggaatct ggtattcatg gggaactgtg tctcctaagt caatcttgct aagtggaaaa    900
cagatttgtt gattagtgca ttaactgtga caataggtgg aatttggtac gtgtatctac    960
agctacattt gtgtacactt gggctttta tacagtattc aaaaaactaa ggctgtgttc    1020
aaaattctct tcctctttag cattcagaaa agcagactga agtgggaact aaaaatgcca   1080
gtgagaaatc tgctgctgca cagagaaaca tagcgttcag ctctaataat tctgtagcaa   1140
agcctctaga gaaaacaacg aaagctgctg ttgaagagac gtcatcagga tcaccaaaaa   1200
tagataagaa aaaagtcct tatggactgt ggatacctgt ctaaaggaaa actaaggggt    1260
tgcctaaaac tgcactttac tgaggggttc gtgtccagca tcagctcacc tgcctgagta   1320
atctcagcag taaatgtgat tgaaatccat tacagaaaga ggcttaatgg tgccgtgttc   1380
atgggtgagg tttctcttga agatgtgagg atacagatga cccagagaat tgcatacagg   1440 tgggggatctt gtacatacct gtaagtattg tatagtatcg cttatataca aaggtgaatt   1500
tttataaaga cacagttgca aactgtattt tgtatatttg ttaataaact ttttgtcttg   1560
atttttatgg aac                                                      1573
```

<210> SEQ ID NO: 13
<211> LENGTH: 438
<212> TYPE: DNA
<213> ORGANISM: Rattus norvegicus
<220> FEATURE:
<221> NAME/KEY:
<223> OTHER INFORMATION: 700251541
<300> PUBLICATION INFORMATION:

<400> SEQUENCE: 13

```
gaccaagaga cctttcaggc ttcaagatat cagggagggc ttcaatgggg cagtggaggg     60
gaggcccatt aatagcagat tatgatgtct ccaattagat gcacctgccc tctggaagtg   120
tggagaccag tattgaaatg gaaagaaaga ctgaatggaa gcccccgag agtagaatga    180 gagagtagaa tgaatggatg agaaaaaaga tttgcattca ctctgggggg agggtgctga   240
ggagccccag ggtcacctga tctcccggga atgaaagggc gggcgaggga gtgatagaaa   300
gtgacaataa ggtgggggag agatgaaaag gggcgcagaa gataataagt gagacaatta   360
agtctaggag agggcttgt ttaacacaac tcatccatat taattcaaaa ttgaggcccc    420
agggatgggc cggagctg                                                 438
```

<210> SEQ ID NO: 14
<211> LENGTH: 313
<212> TYPE: DNA
<213> ORGANISM: Rattus norvegicus
<220> FEATURE:
<221> NAME/KEY:
<223> OTHER INFORMATION: 700280514

```
<300> PUBLICATION INFORMATION:

<400> SEQUENCE: 14
tactgaccta cctcacaggg gtgttgtgag gctttaacta gatgttttgt aaagcgttct      60
gagatacaga gacaaaggcg ccagggaagg gcaaagcatt ctttggactt gaggaagagg     120
aactagtacc ataaacgctg ctattctgag agccatttta aactgcactg ctccacccccc     180 cgcttctcat caccaggaca gcaggtcgag aaatgtcttt ccttgcactt gcttctgggg     240
tttgtgattc ttctaatttt ccccttgct gtatctccct ccttaccccc tccactcgtt     300
ccctgttctg ttt                                                      313

<210> SEQ ID NO: 15
<211> LENGTH: 804
<212> TYPE: DNA
<213> ORGANISM: Rattus norvegicus
<220> FEATURE:
<221> NAME/KEY:
<223> OTHER INFORMATION: 700024124
<300> PUBLICATION INFORMATION:

<400> SEQUENCE: 15
ctcagggact caattctccg cgcgggcgcg gggggaatct taccagggct cttgtctgtc      60
gttcctccag actacacttc ccagaagcct tcgcggccca gacctccttt ggtcttctgc     120
ctaatacatt tcccagaagg aattgcggca gctacggacc ccgatgtacg gagtctaagg     180
ctattgccgc tcccggagtc cattgcggct gacagtgacc actacatttc ccaagagttt     240
cagcagcgac accatccgga agcggtgggc gaattgcgtg tccttgcgcg gcgagtgaag     300
tgagagaccg accatggtgg ctcgagtgtg gtcgctaatg aggttcctca tcaagggaag     360
tgtggctgga ggagcagtct accttgttta tgaccaggag ctgctggggc ctagtgacaa     420
gagcgaggct gtcctggcgg aaggccgagg aagttgtgcc accagcaatg taccagttca     480
gccaatatgt gtgccagcag acgggtctgg agatgtcaca gctcccagcc cctccaaaga     540
ttaactttcc gaacttccgt gattcctgga actcaggcat catctcggtc atggcagcct     600
tgtccgtggc cccctccaag gctcgagaat actccaggga gggctgggag tatgtcaaag     660
aacacaccaa gtaatggatg ccaccttgcc ccccagcatt atgggagtca agaccaagat     720
gccacagaca tcccagcggg gacctcactc tttgcaaagc ttccagcatt gctggcccaa     780
taaaggacat gggatggtca aaaa                                           804
```